United States Patent [19]

McCapra

[11] Patent Number: 5,338,847
[45] Date of Patent: Aug. 16, 1994

[54] HYDROLYTICALLY STABLE CHEMILUMINESCENT LABELS AND THEIR CONJUGATES, AND ASSAYS THEREFROM BY ADDUCT FORMATION

[75] Inventor: Frank McCapra, Seaford, Great Britain

[73] Assignee: London Diagnostics, Inc., Eden Prairie, Minn.

[21] Appl. No.: 860,001

[22] Filed: Mar. 30, 1992

Related U.S. Application Data

[63] Continuation-in-part of Ser. No. 140,040, Dec. 31, 1987, abandoned, and a continuation-in-part of Ser. No. 291,843, Dec. 29, 1988, abandoned, and a continuation-in-part of Ser. No. 418,956, Oct. 10, 1989, abandoned.

[51] Int. Cl.⁵ .................. C07D 219/02; C07D 219/04
[52] U.S. Cl. ..................... 546/104; 436/501; 530/409; 544/355; 546/61; 546/79; 546/93; 546/102; 546/107; 546/108; 546/112; 546/147; 546/170; 548/309.4
[58] Field of Search ............ 546/79, 93, 102, 104, 546/107, 108, 61, 112, 147, 170; 436/501; 530/409; 544/355; 548/309.4

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,932 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

Described are a class of chemiluminescent compound characterized by the presence an aryl ester, thioester or amide of a carboxylic acid substituted heterocyclic ring that is susceptible to chemical attack (such as by oxidic attack) to dissociate the heterocyclic ring to a transient compound. The heterocyclic ring is ring carbon-bonded to the carbonyl of the ester, thioester and amide moiety and possesses a heteroatom in an oxidation state that allows chemiluminescence by dissociating a compound ("intermediate") that decays to produce chemiluminescence, at the carbon bonded to the carbonyl. The aryl ring or ring system is ring carbon-bonded to the oxygen, sulfur or nitrogen of the ester, thioester or amide, as the case may be, and contains at least three substituents on a six-member ring. The substitution on the six-member ring comprises three or more groups acting in concert to sterically and electronically hinder hydrolysis of the ester, thioester or amide linkage. Significant to this invention is the presence of diortho electron donating substitution on the aryl unit in conjunction with meta and/or para substituents that possess a specific level of electron withdrawing capacity. That specific level of electron withdrawing capacity is a $\sigma_p$ value greater than 0 and less than 1. In addition, there is the presence of an adduct affixed at the carbon atom of the heterocyclic ring to which the ester, thioester or amide carbonyl carbon is directly bonded.

Also in accordance with the present invention are conjugates of the labeling composition, assay systems utilizing the conjugates, and assay kits incorporating such chemiluminescent labels.

15 Claims, No Drawings

HYDROLYTICALLY STABLE CHEMILUMINESCENT LABELS AND THEIR CONJUGATES, AND ASSAYS THEREFROM BY ADDUCT FORMATION

RELATED APPLICATIONS

This application is a continuation-in-part of application Ser. No. 140,040, filed Dec. 31, 1987, now abandoned, copending application Ser. No. 291,843, filed Dec. 29, 1988, now abandoned, and copending application Ser. No. 418,956, filed Oct. 10, 1989, now abandoned

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclic esters, thiolesters and amides by adduct formation with the heterocyclic ring.

BACKGROUND TO THE INVENTION

The literature describes classes of compounds that give off light or "luminesce" by reaction through chemical treatment. The compounds that have this capability are termed chemiluminescent materials. Their dissociation is typically caused by treatment with peroxide or molecular oxygen at high pH. Light is produced by the decay of the transient ("intermediate") structure formed by peroxide or molecular oxygen reaction at an $sp^2$ or $sp^3$ hybridized carbon in the compound that is part of a chain or a ring or ring system.

As the literature indicates, any series of reactions which produce the intermediate:

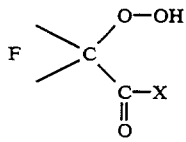

will lead to moderate to strong chemiluminescence. Ⓕ is a structure such that the product carbonyl derivative Ⓕ>C=O is fluorescent and X is a good leaving group, usually with XH, for efficient chemiluminescence, having a $pK_a$ of about $\leq 11$, preferably $<11$, and most preferably, from about 5 to about 8. The reaction may require base catalysis. The intermediate can be prepared (in isolable or transient form, depending on Ⓕ) from species such as:

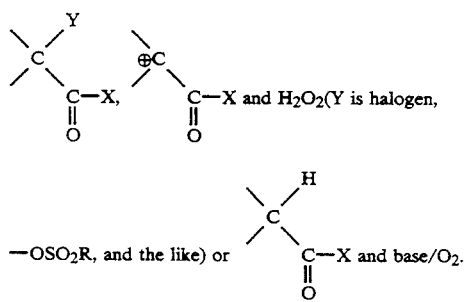

See *Endeavour*, 23, No. 117 (1973) p. 140, *The Chemistry of Bioluminescence* in "Bioluminescence in Action" (P. J. Herring, ed.), Academic Press, London, 1978 (pp. 64–5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

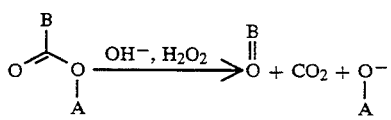

where A is an aryl ring or system and B is a heterocyclic ring or ring system. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149–158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664–1668 (1985); McCapra, "The Application of Chemiluminescence in Diagnostics," 40th Conference of the American Association of Clinical Chemists, New Orleans, LA, Jul. 28, 1988; McCapra, "The Chemiluminescence Of Organic Compounds," Quarterly Reviews, vol. 20, pp. 485–510 (1966); McCapra, "The Chemiluminescence Of Organic Compounds," *Pure and Applied Chemistry*, vol. 24, pp. 611–629 (1970); McCapra, "The chemistry of bioluminescence," *Proceedings Of Royal Society*, vol. B215, pp. 247–278 (1982); McCapra and Beheshti, "Selected Chemical Reactions That Produce Light," *Bioluminescence and Chemiluminescence; Instruments and Applications*, CRC Press, vol. 1, Chapter 2, pp. 9–37 (1985); McCapra, "Chemiluminescent Reactions of Acridines," Chapt. IX, *Acridines*, R. M. Acheson, Ed., pp. 615–630, John Wiley & Sons, Inc. (1973); McCapra, "Chemical Mechanisms in Bioluminescence," *Accounts Of Chemical Research*, vol. 9, no. 6, pp. 201–208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. However, they lose their luminescence capability over time in an aqueous system because they hydrolyze to products that are not available to the assay.

It is well understood in chemistry that carboxylic acid esters, thiolesters and amides are susceptable to hydrolytic attack under acidic or basic conditions resulting in the formation of the carboxylic acid and the hydroxy, mercapto or amino component that is the theoretical or actual precursor to the ester, thiolester or amide. Hydrolysis is more pronounced under greater acidity or basicity. It is also recognized in chemistry that certain levels of hydrolysis can be inhibited by the inclusion of bulky groups that chemically sterically hinder those linkages, see Nishioka et al., *J. Org. Chem.*, vol. 40, no. 17, pp. 2520-2525 (1975), Fujita, et al., "The Analysis of the Ortho Effect," *Progress in Physical Organic Chemistry*, 8, pp. 49-89 (1976), Morrison and Boyd, *Organic Chemistry*, 5th Ed., pp. 842-843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids *are* esterified, the esters are difficult to hydrolyze." (Emphasis in the original)

The difficulty in esterification is not the same in making esters from 2,6-substituted phenols, but the general principles described by March are applicable to enhancing the hydrolytic stability of the resultant ester so long as the ortho substitutions are electron donating.

The functional electron withdrawing or electron donating characteristics of a group in an organic compound is conventionally measured relative to hydrogen. This relative ranking accepts that all groups on a molecule will provide some slectron withdrawing effect, and distinguishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, *Advanced Organic Chemistry*, 3rd Edition, Publ. by John Wiley & Sons, New York, N.Y. (1985) at pp. 242-250 and 617-8. Tables of $\sigma_p$ values for various groups can be found in Hansch et al., *J. Med. Chem.* 16(11): 1209-1213 (1977) and Hansch and Leo, "Substituent Constants for Correlation Analysis in Chemistry and Biology," Ch. 6, pp. 49-52 (John Wiley & Sons, New York 1979). The $\sigma_p$ values reported in the Hansch articles are relied on herein in characterizing relative values for groups both in the meta and para position.

The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclo esters, thiolesters and amides by virtue of adducting the heterocyclic ring.

The invention may be characterized by the inclusion of an adduct at the carbon position of the heterocyclic ring to which the ester, thiolester and amide is bonded. Such adduct formation inhibits the hydrolysis of ester, thiolester and amide group.

In a preferred embodiment of the invention, the chemiluminescent compound of the invention is characterized by the presence an aryl ester, thiolester or amide of a carboxylic acid substituted heterocyclic ring that is susceptible to chemical attack (such as by oxidic attack) to form a transient compound from the heterocyclic ring. The heterocyclic ring is ring carbonbonded to the carbonyl of the ester, thiolester and amide moiety and possesses a heteroatom in an oxidation state that allows chemiluminescence by dissociating a compound ("intermediate") that decays to produce chemiluminescence, at the carbon bonded to the carbonyl. The aryl ring or ring system is ring carbon-bonded to the oxygen, sulfur or nitrogen of the ester, thiolester or amide, as the case may be, and contains at least three substituents on a six-member ring. The substitution on the six-member ring comprises three or more groups acting in concert to sterically and electronically hinder hydrolysis of the ester, thiolester or amide linkage. Significant to this invention is the presence of diortho electron donating substitution on the aryl unit in conjunction with meta and/or para substituents that possess a specific level of electron withdrawing capacity. That specific level of electron withdrawing capacity is a $\sigma_p$ value greater than 0 and less than 1. It is this combination that causes the chemiluminescent label compound to have uniquely high hydrolytic stability that is superior to the use of meta and/or para substituents that possess a $\sigma_p$ value of 0 and less than 0 or 1 and greater than 1. In addition, the invention contemplates the presence of an adduct affixed at the carbon atom of the heterocyclic ring to which the ester, thiolester or amide carbonyl carbon is directly bonded.

Also in accordance with the present invention are conjugates of the labeling composition, assay systems utilizing the conjugates, and assay kits incorporating such chemiluminescent labels.

In particular, this invention relates to a heterocyclic composition capable of chemiluminescent properties when labeled to a specific binding material, by reaction with acid, then peroxide or molecular oxygen, comprising
(a) an aryl ring,
(b) an ester, thiolester or amide linkage moiety with enhanced hydrolytic stability, and
(c) a heterocyclic organic ring moiety,
  in which
    (i) the carbonyl carbon of (b) is covalently bonded to a carbon atom (x) of (c) and the remaining free valence of (b) is carbon bonded to an aromatic ring carbon atom (y) of (a),
    (ii) (a), (c) or both contain at least one sterically-hindering substituent group on the ring carbon atoms adjacent to one or more of (x) and (y),
    (iii) a monovalent moiety is bonded directly to carbon atom (x),
    (iv) at least one of (a) and (c) contains a functional group
      (1) directly or indirectly bonded to a ring carbon other than said adjacent carbon atoms to (x) or (y), and
      (2) that is complementary for reaction with a moiety in the specific binding material to effect a heterolytic or homolytic reaction therewith
    (v) (a) contains one or more substituent groups having a $\sigma_p$ value greater than 0 and less than 1 bonded to ring carbon atoms thereof other than those adjacent to (y), and
    (vi) (c) contains
      (1) at least one ring carbon atom adjacent to said ring carbon atom (x), and
      (2) a ring member heteroatom in an oxidation state that provides such chemiluminescence properties.

In another embodiment, the invention relates to a conjugate possessing chemiluminescent properties by reaction of acid therewith, followed by molecular oxygen or a peroxide, comprising a chemiluminescent label bonded to a specific binding material that contains
(a) an aryl ring
(b) a sterically-hindered ester, thiolester or amide linkage moiety with enhanced hydrolytic stability, and
(c) a heterocyclic organic ring, in which
  (i) the carbonyl carbon of (b) is covalently bonded to a carbon atom (x) of (c) and the remaining free valence of (b) is carbon bonded to an aromatic ring carbon atom (y) of (a),
  (ii) (a), (c) or both contain at least one sterically-hindering substituent group on the ring carbon atoms adjacent to one or more of (x) and (y),
  (iii) a monovalent moiety is bonded directly to carbon atom (x),
  (iv) at least one of (a) and (c) contains a functional group
    (1) directly or indirectly bonded to a ring carbon other than said adjacent carbon atoms to (x) or (y), and
    (2) that is complementary for reaction with a moiety in the specific binding material to effect a heterolytic or homolytic reaction therewith
  (v) (a) contains one or more substituent groups having a $\sigma_p$ value greater than 0 and less than 1 bonded to ring carbon atoms thereof other than those adjacent to (y), and
  (vi) (c) contains
    (1) at least one ring carbon atom adjacent to said ring carbon atom (x), and
    (2) a ring member heteroatom that is in an oxidation state whereby reaction of molecular oxygen or a peroxide with said composition forms an intermediate which decays to produce chemiluminescence.

The invention includes a method for assaying the presence of an analyte in a sample comprising contacting an analyte with a chemiluminescent labeled specific binding material, inducing chemiluminescence by treating the label with acid, then by decay of an intermediate formable in the presence of peroxide or molecular oxygen, and measuring chemiluminescence therefrom to assay the analyte; wherein the chemiluminescent labeled specific binding material contains
(a) an aryl ring
(b) a sterically-hindered ester, thiolester or amide linkage moiety with enhanced hydrolytic stability, and
(c) a heterocyclic organic ring, in which
  (i) the carbonyl carbon of (b) is covalently bonded to a carbon atom (x) of (c) and the remaining free valence of (b) is carbon bonded to an aromatic ring carbon atom (y) of (a),
  (ii) (a), (c) or both contain at least one sterically-hindering substituent group on the ring carbon atoms adjacent to one or more of (x) and (y),
  (iii) a monovalent moiety is bonded directly to carbon atom (x),
  (iv) at least one of (a) and (c) contains a functional group
    (1) directly or indirectly bonded to a ring carbon other than said adjacent carbon atoms to (x) or (y), and
    (2) that is complementary for reaction with a moiety in the specific binding material to effect a heterolytic or homolytic reaction therewith
  (v) (a) contains one or more substituent groups having a $\sigma_p$ value greater than 0 and less than 1 bonded to ring carbon atoms thereof other than those adjacent to (y), and
  (vi) (c) contains
    (1) at least one ring carbon atom adjacent to said ring carbon atom (x), and
    (2) a ring member heteroatom that is in an oxidation state whereby reaction of molecular oxygen or a peroxide with said composition forms an intermediate which decays to produce chemiluminescence.

The invention also embodies a specific binding assay kit comprising a vial containing a conjugate possessing chemiluminescent properties by reaction therewith of acid, then molecular oxygen or a peroxide, comprising a chemiluminescent label bonded to a specific binding material that contains
(a) an aryl ring
(b) a sterically-hindered ester, thiolester or amide linkage moiety with enhanced hydrolytic stability, and
(c) a heterocyclic organic ring, in which
  (i) the carbonyl carbon of (b) is covalently bonded to a carbon atom (x) of (c) and the remaining free valence of (b) is carbon bonded to an aromatic ring carbon atom (y) of (a),
  (ii) (a), (c) or both contain at least one sterically-hindering substituent group on the ring carbon atoms adjacent to one or more of (x) and (y),
  (iii) a monovalent moiety is bonded directly to carbon atom (x), (iv) at least one of (a) and (c) contains a functional group
  (1) directly or indirectly bonded to a ring carbon other than said adjacent carbon atoms to (x) or (y), and
  (2) that is complementary for reaction with a moiety in the specific binding material to effect a heterolytic or homolytic reaction therewith
(v) (a) contains one or more substituent groups having a $\sigma_p$ value greater than 0 and less than 1 bonded to ring carbon atoms thereof other than those adjacent to (y), and
(vi) (c) contains
  (1) at least one ring carbon atom adjacent to said ring carbon atom (x), and
  (2) a ring member heteroatom that is in an oxidation state whereby reaction of molecular oxygen or a peroxide with said composition forms an intermediate which decays to produce chemiluminescence.

DETAILED DESCRIPTION OF THE INVENTION

The chemiluminescent compounds of the present invention have either of the two following schematic formulae:

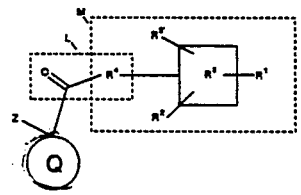

In the schematic formula, the hatched-line box labeled "L" contains the ester, thiolester or amide "linkage" which is carbon-bonded between two substituted rings or ring systems represented by the circle labeled "Q" and the solid box labeled "R³". Whether the linkage L is an ester, thiolester or amide is determined by R⁴ being —O—, —S— or —NT—, respectively. T is a stable nitrogen bonded group such as —SO₂CF₃, to form —N(SO₂CF₃)— and equivalent groups. The preferred linkage is the ester. M encompasses the leaving group comprising a portion of L and moiety R³ with its associated R¹, R² and R²'. M would be the leaving group even if R¹ were conjugated to a specific binding material. The leaving group possesses the typical $pK_a$ of about ≦11.

Q is a heterocyclic ring or ring system to which the ester, thiolester or amide linkage L is attached at a carbon atom within the heterocyclic ring or ring system. That carbon atom (1) is either sp² or sp³ hybridized, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is sp² hybridized, the heteroatom is in a positive oxidation state (i.e., have a positive charge, for example, as obtained by N-alkylation or N-oxidation). If the carbon to which the linkage is attached is sp³ hybridized, the heteroatom is in a neutral oxidation state (i.e., uncharged). When the heteroatom is nitrogen, proper oxidation states can be achieved only if the nitrogen is substituted with an alkyl group (including a functionalized alkyl group), an aryl group (including a functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium. Rings or ring systems in which the heteroatom is in a neutral oxidation state include the reduced forms of the foregoing. These rings or ring systems are derived from the following rings or ring systems:

Acridine Series

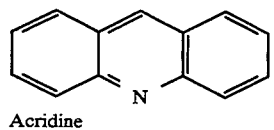

Acridine

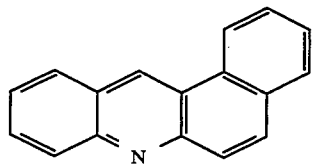

Benz[a]acridine

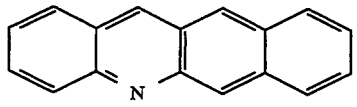

Benz[b]acridine

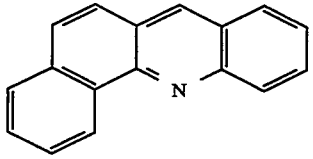

Benz[c]acridine

Azole Series

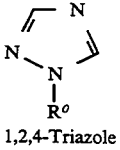

1,2,4-Triazole

Isooxazole

Isothioazole

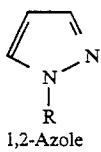
1,2-Azole

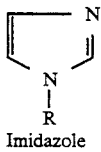
Imidazole

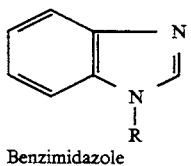
Benzimidazole

Quinoline Series

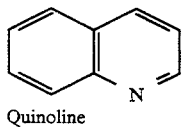
Quinoline

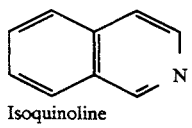
Isoquinoline

Quinolixinium Cations

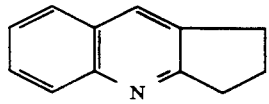

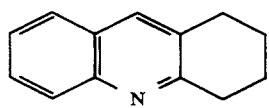

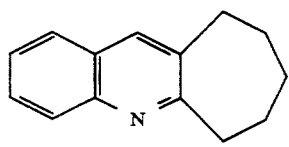
Cyclic C3, C4, C5-Substituted Quinolines

Pyridine/Pyrimidine Series

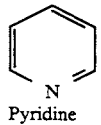
Pyridine

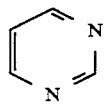
Pyrimidine

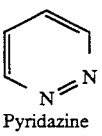
Pyridazine

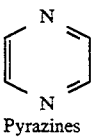
Pyrazines

Miscellaneous

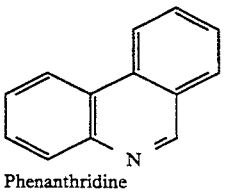
Phenanthridine

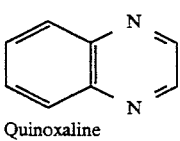
Quinoxaline

The heterocyclic ring or ring system may contain substitutions not shown in the above schematic formula. When the heterocyclic ring or ring system contains substitution, the substitution may be at any position, including the heteroatom. Such rings and ring systems, whether or not substituted, are considered herein to be within the meaning of the term "heterocyclic ring or ring system."

Suitable ring substitutions may be functional or non-functional. Functionality can be for the purpose of enhancing the hydrolytic stability of the compound or for providing coupling capabilities via homolytic or heterolytic reactions or other forms of association that couple the label compound to its substrate. Such substitutions include those for the purposes of producing peri-interactions around the linkage L to enhance its hydrolytic stability, providing functionality to the compound for coupling to proteins and other materials with complementary functionality, and increasing the compound's solubility and chemiluminescent efficiency. Groups useful for associating the compound to proteins and other materials so that the chemiluminescent label compounds of the invention function in a coupled state with them include, but are not limited to, pendant groups on the heterocyclic ring or ring system such as alkyl and functionally substituted alkyl (such as $XR^0$—, wherein X is hydrogen or a functional group such as amino, mercapto, hydroxy, carboxy, and the like, and $R^0$ is alkyl of from 1 to about 18 carbon atoms), alkenyl, alkynyl, alkoxy, alkylamino, aminoalkylamino (such as $XR^0)_{2-n}NH_n$—, where n is 1 or 2, and the like), or alkyloxycarbonyl or optionally functionalized aryl, aralkyl, alkaryl or their ether bridged analogs. For example, the aryl groups can be directly joined to the heterocyclic ring or ring system or indirectly joined by a number of units, such as oxy, sulfide, sulfoxide, sulfone, amino, alkylene, alkenylene, alkynylene, alkylamino and aminoalkyl, oxyalkyl and alkoxy, thioalkyl and alkylsulfide, and alkyloxycarbonyl, to illustrate a few. The following groups illustrate the variety that such functionality can take:

—CO₂R⁶, where R⁶ is hydrogen, alkyl or aryl

—C=NH₂, where R⁷ is a residue of an alcohol
|
OR⁷

—SO₂Cl

—NCS

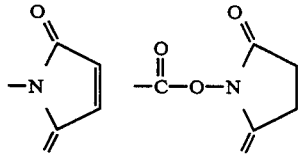

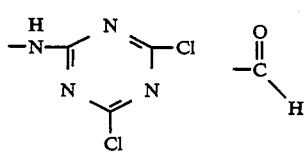

—N(CH₃)₂(CH₂)$_m$Cl, where m is equal to or greater than 1

—N₃ and other photolabile functionalities

—NH₂ or oniums (such as quaternary ammoniums, phosphoniums, sulfoniums, and the like), sugars, polyalkylenepolyamines and polyalkyleneoxide (e.g., polyoxyethylene, polyoxy-1,2-propylene, polyoxy-1,3-propylene, polyoxy-1,2-butylene, etc.), and the like. Other chains, groups and functionalities useful for attaching compounds of the present invention to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

Peri substituents, which can cause peri-interactions, include any group which can cause steric hindrance with respect to the carbon to which the ester, thioester of amide linkage is attached and/or with respect to the carbon within the ester, thioester of amide linkage. Preferred peri substituents include short alkyl groups (e.g., methyl, ethyl, and the like), aryl groups (e.g., phenyl), alkaryl (e.g., tolyl, xylyl, and the like), alkoxyalkyl (e.g., methoxymethyl, ethoxyethyl, and the like). The peri substituents, if present, are located on carbon atoms within the heterocyclic ring or ring system which are "adjacent to" the carbon to which the ester, thioester or amide linkage is attached. Moieties can include more than one peri substituent. For example, peri substituents can be placed in the following positions:

(a) in acridiniums and acridans: on C₁ and C₈;

(b) in phenanthridiniums and reduced phenanthridiniums: on C₇; and (c) in quinoliniums and reduced quinoliniums: on C₃.

The aryl ring or ring system, represented by R³, includes at least one substituted six-member ring of the formula

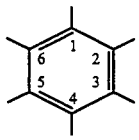

in which the substituents comprise at least one R¹ at ring carbons 3, 4 and 5, and R² and R²′ at ring carbons 2 and 6. The ester, amide or thioester linkage is directly attached through a covalent bond to such six-member ring at ring carbon 1. R³ may include but is not limited to phenyl, naphthyl and anthracyl, which are derivatives of the following structures:

Phenylene

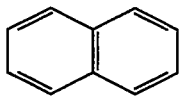

Naphthalene

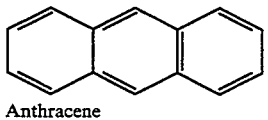

Anthracene

In those cases where napthyl or anthracyl rings are employed, one of the rings constitutes R³ and the other ring or rings are formed in combination with any adjacent set of ring carbons thereof other than carbon 1. R³ linked through carbon 1 may be substituted at any aromatic carbon position provided carbon atoms 2 and 6 are appropriately substituted and one or more of carbons 3, 4 and 5 are appropriately substituted with a group having a σ$_p$ value greater than 0 and less than 1. In the broadest sense of the invention, R³ may include, but not limited to, the substituent groups designated for R¹, R² and R²′ described below. R³ may be attached through substituents R¹, R² and R²′ to protein or other material. Appropriate groups for such purpose are discussed above.

R² and R²′ are bulky groups which are located on R³ at C₂ and C₆ so as to sterically hinder, in the traditional manner, the hydrolysis of the linkage L between R³ and the heterocyclic ring or ring system Q. Where R³ is phenyl with the ester linkage being attached at position 1, R² and R²′ are located at the ortho 2 and 6 positions. R² and R²′ may be the same or different, and either may include:

an alkyl (C₁₋₄) or optionally functionalized alkyl (C₁₋₄) group an aryl or optionally functionalized aryl group —OR, where R is alkyl (C₁₋₄) or aryl —SR, where R is alkyl (C₁₋₄) or aryl.

The required steric hindrance can also be provided by other rings within a multi-ring R³ which are "adjacent" to the six-member ring to which the ester linkage is attached. For example, if R³ is naphthyl and an ester linkage is attached at the 1 position, R² could be a methyl group at the 2 position and R²′ is the "adjacent"

ring containing carbons 7–10. In such cases, the adjacent ring is considered herein to be a substitution (on the six-member ring within $R^3$) which sterically hinders the hydrolysis of the linkage.

In a preferred embodiment of the invention, $R^2$ and $R^{2'}$ are groups that are regarded to be electron-donating. The preferred groups are alkyl, aryl, alkoxy, aryloxy, and the like.

$R^1$ can be one or more groups located on $R^3$ in the meta and/or para positions relative to the linkage L on the aromatic ring. It is any electron withdrawing group that possesses a $\sigma_p$ value greater than 0 and less than 1.

$R^1$ in the preferred embodiment, possesses two (2) qualities: (1) when bonded to the aryl group $R^3$, it has the desired $\sigma_p$ value; and (2) it has a capability of bonding to an active hydrogen containing group such as amino, amido, carboxyl, hydroxyl, thiol, and the like. The bonding capability of $R^1$ need only be sufficient to link the label compound to the active hydrogen containing group. Such bonding may be covalent, ionic, hydrogen and other associative bonding that would be acceptable for linking with the composition containing the active hydrogen to which bonding is desired.

Particularly desirable $R^1$ groups are those that are directly bonded to the $R^3$ ring $C_{3,4 \ and/or \ 5}$ atoms through a non-carbon and non-oxygen unit. The preferred $R^1$ groups contain non-carbon and non-oxygen radicals such as N, S, P, B, Si, and the like, bonded to one or more of the $C_{3,4 \ and/or \ 5}$ atoms or substituted alkoxy and alkyl possessing the desired $\sigma_p$ value. Each of these preferred groups frequently contain one or more of oxo (i.e., =O), oxy (i.e., —O—), halogen, and carbon bonded organic moieties bonded thereto. When all of the free valences of the radicals are saturated with carbon bonded organic, then the group is an onium, such as quaternary ammonium, sulfonium, phosphonium, and the like. To the extent that organic substitution on the radical creates a group having a $\sigma_p$ value outside of the desired range, then such substitution is outside the practice of the invention. Desirable electron withdrawing groups include those designated above with respect to the functional groups associated with the heterocyclic moiety to the extent they satisfy the recited $\sigma_p$ value limitation, as well as the following:

—NO$_2$

—SO$_2$-halogen

—Br

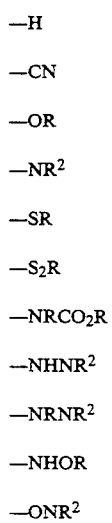

—N(CH$_3$)$_3^+$

—B(OH)$_2$

—CF$_3$

—SO$_2$CH$_3$

—OCF$_3$

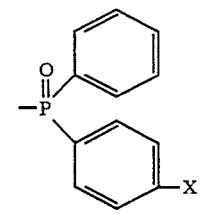

in which halogen may be fluorine, chlorine, bromine and iodine, chlorine being the most preferred, X is a functional group reactive with active hydrogen, such as carboxyl, sulfonyl, and amino. NO$_2$, —SO$_2$Cl, —Br, and —N(CH$_3$)$_3^+$ are particularly preferred. Most preferred are NO$_2$ and —SO$_2$Cl, the former for the uniquely high hydrolytic stability it confers on the label, per se or when conjugated, and the latter for the exceptional bonding to proteins, forming stable sulfonamide bonds, and the superior hydrolytic stability conferred to the label, per se or when conjugated.

As noted above, covalent or ionic attachment to proteins and other materials can be effected through substitutions on $R^3$ or Q. Some of the electron withdrawing groups $R^1$ are particularly effective for that purpose. Of the preferred electron withdrawing groups, —SO$_2$Cl is exceptionally effective for attaching a chemiluminescent moiety to protein or other active hydrogen containing material. The resulting sulfonamide is possessed of the desired $\sigma_p$ value. A conjugate so formed is a particularly desirable embodiment of the invention. Alternatively, any of the groups listed above for attachment to the heterocyclic ring or ring system Q can also be used to the extent they can be attached as substituents of $R^3$ and provide the desired $\sigma_p$ value. Methods of joining such attaching groups to protein and other materials utilizing covalent bonding or weaker chemical forces are well known in the art.

In schematic formula above, Z is a secondary substituent group attached to the carbon atom to which the ester, thioester or amide linkage is attached when such carbon atom is sp$^3$ hybridized. Z may include but is not limited to:

—H

—CN

—OR

—NR$^2$

—SR

—S$_2$R

—NRCO$_2$R

—NHNR$^2$

—NRNR$^2$

—NHOR

—ONR$^2$

Generally, in addition to a hydrogen and a halogen, Z can be any nucleophilic group of the general formula R$_n$X, where X is O,N, S or C (with appropriate changes in n to accommodate valence changes in X) and where R is any substituent (preferably, alkyl, aryl, an amino acid or a sugar, optionally substituted) containing X as a component thereof.

$R_n$ and $R_nX$ can also be (or be derived from) a drug or steroid molecule. In compounds in which Z is $R_nX$, Z serves as a "blocking" moiety which prevents or deters hydrolysis of the ester, thioester or amide linkage, thus decreasing the likelihood that such compounds will be unstable. The blocking effect is caused by (1) the steric bulk of the $R_nX$ group which physically blocks attack by chemical species which would induce or increase hydrolysis of the ester, thioester or amide linkage (e.g., species which would form a pseudo base at carbon 9 of an acridinium compound), and (2) electronic effects produced by the change of the carbon atom from $sp^2$ to $sp^3$ hybridization (which cause the ester, thioester or amide linkage to behave more like an aliphatic ester, thioester or amide). When compounds including an $R_nX$ group are triggered to produce chemiluminescence they must first be treated with acid which cleaves the $R_nX$ group, thus allowing induction of the chemiluminescent reaction upon the addition of peroxide, base or other triggering agent (acid treatment is not required for compounds where Z is —H or a halogen). The character and structure of the $R_nX$ group is limited by only two factors: (1) the size of the $R_nX$ group must be such that the group can be added to compounds of the present invention during synthesis as described below or by other synthetic procedures (i.e., the $R_nXH$ species, from which the $R_nX$ group derives during synthesis, cannot be so large that steric effects make it impossible to synthesize a compound of the present invention having such $R_nX$ group), and (2) the $R_nX$ group must be of a steric and chemical character such that it can be cleaved from the molecule with acid before triggering the chemiluminescent reaction.

Other compounds of the present invention have the following schematic formula:

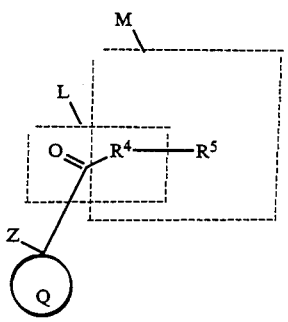

II.

where Q, Z, L, M and $R^4$ are as described above. In addition to the moieties wherein $R^5$ equals $R^1+R^2+R^{2'}+R^3$ (as previously described as in the first schematic formula), preferred moieties of the included moieties where $R^5$ equals an aryl ring or ring system which is substituted or unsubstituted. These moieties can also include peri substituents as previously described. Phenyl-N-methyl-1,3-dimethyl-acridan-9-methoxy-9-carboxylate, which has the following formula:

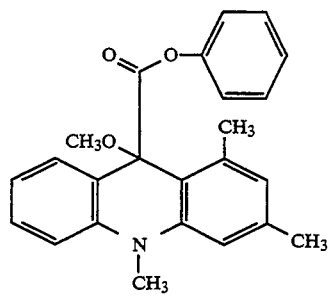

is a preferred moiety which has an $Z/R_nX$ group ($CH_3O$— on $C_9$), has a peri substituent ($CH_3$— on $C_1$) and is an unsubstituted phenyl ester.

Another group of compounds of the present invention have the following schematic formula:

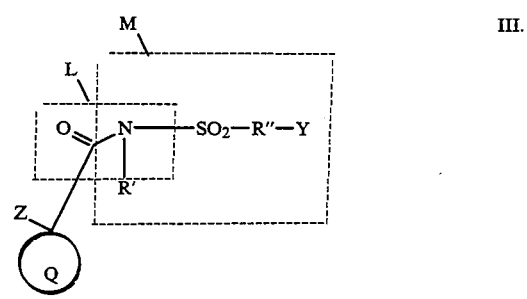

III.

where Q, M, Z and L are as described above, where R' and R'' are selected from the group consisting of alkyl, alkylene, aryl, optionally substituted alkyl, optionally substituted alkylene, optionally substituted aryl, alkyloxy, aryloxy, halo, optionally protected amino, substituted aminohydroxy, protected hydroxy, oxo, thio, imino, optionally substituted mercapto, a heterocyclic ring, and a heteroalkyl group, and where Y is selected from the group consisting of a hydrogen, carboxy, carbonyl halide, sulfonyl halide, carboalkoxy, carboxamido, carboaryloxy, cyano, carboximido, isocyanato, isothiocyanate, sulfo, N-succinimidylcarboxy and N-maleimide. Such moieties can also include peri substituents as previously described.

Still another group of compounds of the present invention have the following schematic formula:

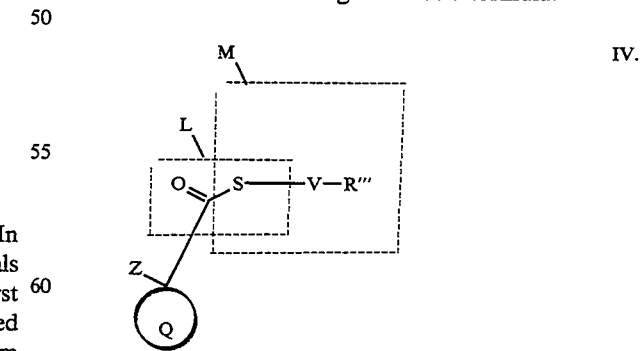

IV.

where M, as defined above, comprising V-R''' is the leaving group; Q, Z and L are as described above; V is an aliphatic or aromatic group; and R''' is a group which is useful for attaching the compound to protein or other specific binding partners (as previously described). Such compounds can also include peri substituents as previously described.

One further group of compounds of the present invention have the following schematic formula:

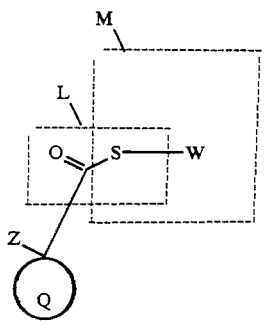

where Q, Z, M and L are as described above, M comprises W in the leaving group and where SW is a sulfonamido or sulfocarbonyl group. Such compounds can also include peri substituents as previously described.

A still further group of compounds of the present invention include an alternative to linking the above compounds through the aryl ring or ring system. The foregoing compounds can generally be linked through the nucleus, i.e. the heterocyclic ring or ring system. This linkage can occur, for example, on the benzene rings or nitrogen at the ten (10) position (N-10) of acridinium moieties.

The novel esters, thioesters and amides of the invention are produced by conventional procedures in the art. For an example, a heterocyclic acyl halide of the formula

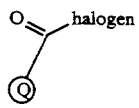

may be reacted with an aromatic 1-hydroxy, 1-mercapto or 1-amino containing the desired diortho (2,6) substitution, to form the desired L linkage. In some cases, the aromatic hydroxy, mercapto or amine will contain as well, the $R^1$ functionality. In other cases, it will be necessary to react the resultant esters, thioesters and amides with reagents suitable for introducing the $R^1$ functionality. For example, chlorosulfonation will introduce the chlorosulfonyl groups. Its concentration in the reaction medium can be amplified by subsequent chlorination with a chlorinating agent such as thionyl chloride.

In many cases, the reactions will proceed to the formation of intermediates that require separation for the next reaction step or final products that require isolation. In such cases, conventional techniques such as distillation, extraction, crystallization, washing and the like, will be required. Conventional separation by the addition of non-solvent to a solvent solution to force precipitation of a desired material is frequently found useful.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3.964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of (i) treating the chemiluminescent moiety with acid to cleave a Z (i.e., $R_nX$) group from the moiety, and/or (ii) triggering the chemiluminescent moiety to chemiluminesce in the case of those assay formats in which the formation of the reaction products does not itself trigger the chemiluminescent moiety.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields characterize the extent reactants are consumed unless indicated otherwise.

EXAMPLE 1

Illustrative of the present invention is (2,6-dimethyl-4-nitro)phenyl-3-(3-succinimidyloxycarbonyl)-propyloxy-9,10-dihydro-N-methyl-acridan-9-carboxylate which has the following formula:

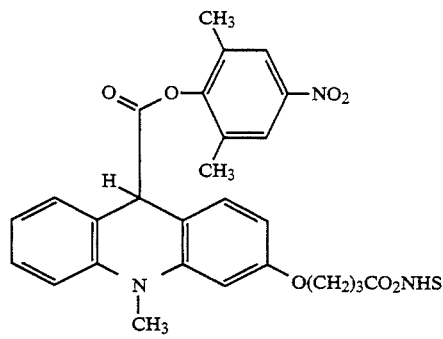

The compound (2,6-dimethyl-4-nitro)phenyl-3-(3-succinimidyloxycarbonyl)propyloxy-9,10-dihydro-N-methyl-acridan-9-carboxylate was synthesized from the acridinium acid (9). Reduction of the acid (9) with sodium cyanoborohydride gives the acridan which is then converted to the NHS ester by the mixed anhydride method. These reactions are described in further detail in the following.

The acridinium acid (9) (210 mg, 0.37 mmole) was dissolved in a 1:1 mixture of acetonitrile and 0.1M phosphate buffer, pH 5.2 (60 ml). A solution of sodium cyanoborohydride (190 mg) in acetonitrile (5 ml) was added dropwise to the acridinium solution. This results in the bleaching of the yellow color of the solution. Stirring was continued for 15 minutes. Acetonitrile (100 ml) was added and the solvents were removed in a rotary evaporator. The residue as a suspension in water is extracted with ethylacetate. The organic layer was washed with water and dried. Removal of solvents gave (2,6-dimethyl-4-nitro)phenyl-3-(3-carboxyl)propyloxy-9,10-dihydro-acridan-9-carboxylate (yield=90%).

The acridan acid (125 mg, 0.255 mmole) and N-methylmorpholine (28 l) were dissolved in anhydrous acetonitrile (15 ml). The mixture was cooled in a $CCl_4$/dry ice bath under nitrogen. Isobutylchloroformate (35 µl) was added, the mixture was stirred for 3 minutes and N-hydroxysuccinimide (35 mg) dissolved in acetonitrile (2 ml) was added. After stirring at $-20°$ C. for 15 minutes the $CCl_4$/dry ice bath was removed and the reaction allowed to warm up to room temperature. After 2 hours the solvents were evaporated and the residue extracted into ethyl acetate. The insoluble N-methylmorpholine hydrochloride salt was removed by filtration. The filtrate was concentrated and hexane (20 ml) was added. Cooling results in crystallization of (2,6-dimethyl-4-nitro)phenyl-3-(3-succinimidyloxy-carbonyl)propyloxy-9,10-dihydro-N-methyl-acridan-9-carboxylate. The crystals were finally filtered and washed with hexane (yield=70%). MS: FAB, dithiothreitol/dithioerythrytol matrix, 588 (M+ +1). HPLC: Waters C18 Novapak (3.9 mm×15 mm) (commercially available from Millipore Corporation, Waters Chromatography Division, Milford, Massachusetts), $CH_3CN/H_2O$ (0.1% trifluoracetic acid) 60:40, flow rate 1.0 ml/min, retention time 6.34 min, detected at 280 nm.

EXAMPLE 2

Another moiety of the present invention is (2,6-dimethyl-4-nitro)phenyl-5,6-dihydro-N-methyl-phenanthridinium-6-carboxylate fluorosulfonate which has the following formula:

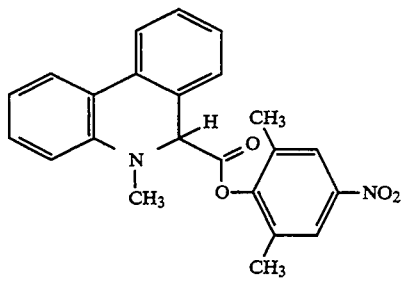

The compound (2,6-dimethyl-4-nitro)phenyl-5,6-dihydro-N-methyl-phenanthridinium-6-carboxylate fluorosulfonate is synthesized from the unreduced phenanthridinium analog (27) of the preceding example. The phenanthridinium (27) (398 mg, 0.8 mmole) was dissolved in a 1:1 mixture of acetonitrile and 0.1M phosphate buffer, pH 5.2 (80 ml). A solution of sodium cyanoborohydride (410 mg) in acetonitrile (10 ml) was added dropwise to the phenanthridinium solution. This resulted in the bleaching of the yellow color of the solution. Stirring was continued for 15 minutes. Acetonitrile (100 ml) was added and the solvents were removed in a rotary evaporator. The residue was suspended in water and extracted with ethylacetate. The organic layer was washed with water and dried. Removal of solvents gave (2,6-dimethyl-4-nitro)phenyl-5,6-dihydro-N-methyl-phenanthridinium-6-carboxylate fluorosulfonate (yield=90%).

EXAMPLE 3

A conjugate of the present invention comprises progesterone bound to a β-D-thioglucose adduct of (2,6-dimethoxy-3-chlorosulfonyl)phenyl-N-methyl-acridinium-9-carboxylate fluorosulfonate. The progesterone conjugate of the β-D-thioglucose adduct of (2,6-dimethoxy-3-chlorosulfonyl)phenyl-N-methyl-acridinium-9-carboxylate fluorosulfonate has the following formula:

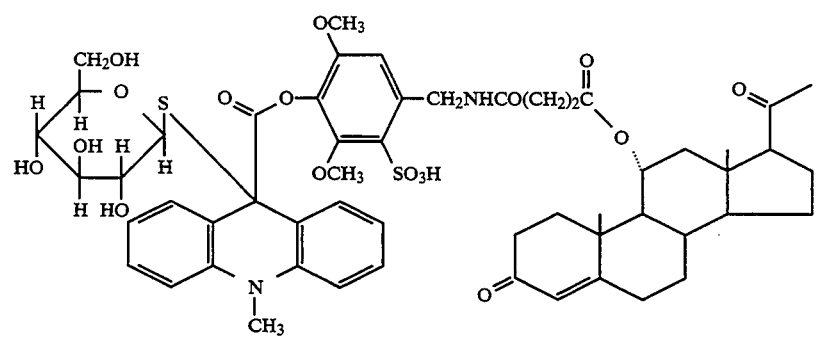

The progesterone conjugate is synthesized according to the following scheme:

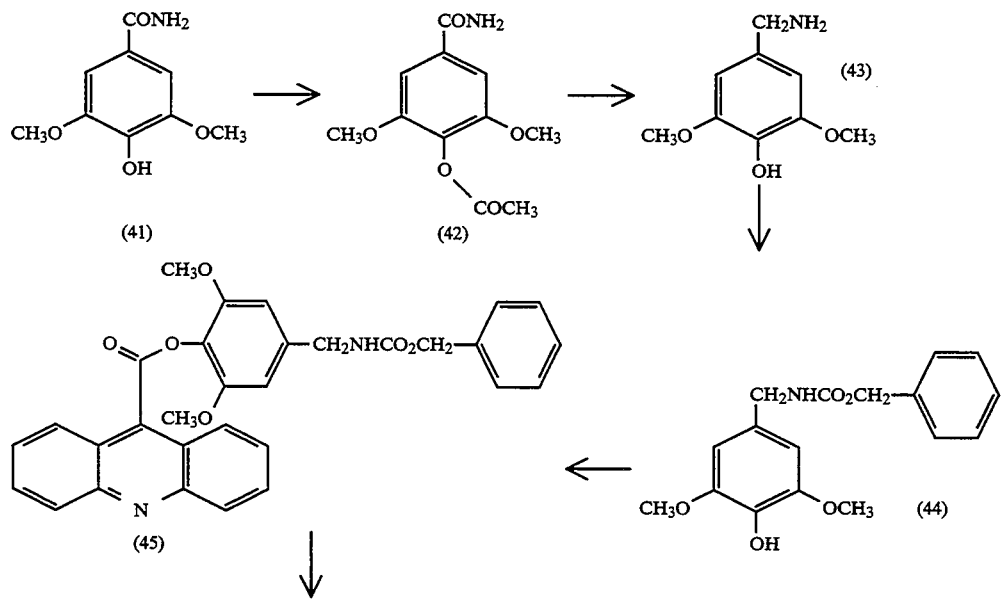

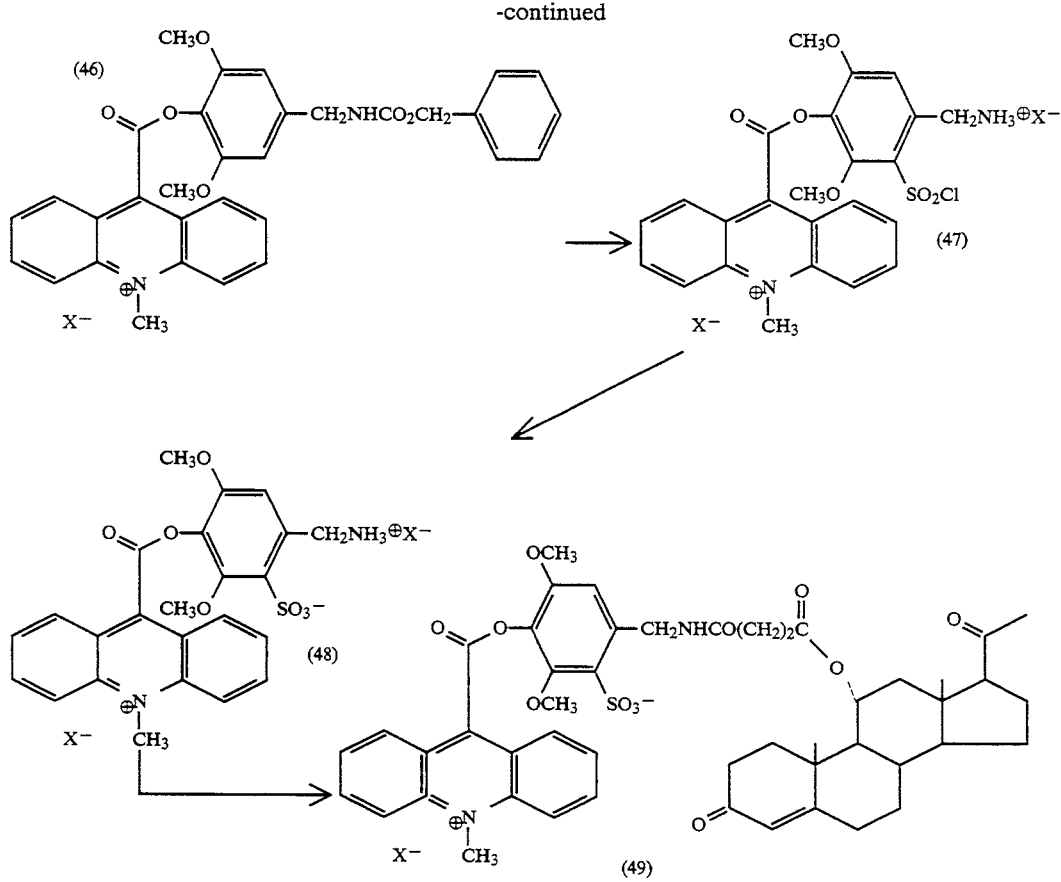

In the reaction scheme, 3,5-dimethoxy-4-hydroxy benzamide (41) (3.0 g, 15.2 mmole) was dissolved in anhydrous pyridine (15 ml) and the solution was cooled in a dry ice/CCl₄ bath. Acetyl chloride (1.4 ml, 1.54 g, 19.7 mmole) was added and the mixture was kept stirred at room temperature for 2 hours. Methanol (1 ml) and water (5 ml) were added and the solvents were removed under reduced pressure. The residue was treated with water (50 ml) acidified with dilute hydrochloric acid and was extracted with ethyl acetate. Washing with water, drying and evaporating of the ethyl acetate gave 2,6-dimethoxy-4-carboxamido-phenyl acetate (42) (2.2 g) which was recrystallized from ethyl acetate (yield=60%).

The phenyl acetate (42) (1.27 g, 5.33 mmole) was dissolved in anhydrous tetrahydrofuran (125 ml). Diborane solution in THF (1.0M, 10.9 ml, 10.9 mmoles) was added and the mixture was refluxed for 4 hours. After cooling to room temperature water (2 ml) and hydrochloric acid (1.0N, 5 ml) were added. After stirring for 30 minutes the solvents were removed in vacuum. The residue was extracted with chloroform. The chloroform was then dried and removed in vacuo. 2,6-dimethoxy-4-aminomethylphenol (43) was used in the next step without further purification.

To a solution of the crude amine (43) in anhydrous pyridine (10 ml) benzylchloroformate (1.050 ml, 1.25 g, 7.3 mmole) was added and the mixture was stirred for 3 hours at room temperature. Water (5 ml) was added and the solvents were removed in vacuo. To the residue water (30 ml) was added and the mixture was acidified with dilute HCl. Extraction with ethyl acetate, washing with water, drying and evaporation of the solvent gave 2,6-dimethoxy-4-(benzyloxycarbonylamino)methyl phenol (44) as an oil (yield=70% overall).

Acridine-9-carboxylic acid (754 mg, 3.38 mmole) was dissolved in anhydrous pyridine (14 ml). p-Toluene sulfonyl chloride (1.28 g, 6.76 mmole) was added and the mixture was stirred at room temperature for 30 minutes. 2,6-dimethoxy-4-(benzyloxy carbonylamino)-methyl phenol (44) (1.18 g, 3.76 mmole) was added and the mixture was stirred at room temperature for 15 hours. Water (10 ml) was added and solvents were removed in vacuo. The residue was dissolved in chloroform and the chloroform layer was washed successively with water, 0.1N HCl and sodium bicarbonate solution. Drying and evaporating of chloroform gave the crude ester which was chromatographed on a silica gel column using CHCl₃/Ethyl acetate, 1:1. as the solvent. Evaporation of the solvents from the pooled fractions gave [2,6-dimethoxy-4-(benzyloxycarbonylamino)methyl]phenyl-acridine-9-carboxylate (45) (yield=22%).

The acridine (45) (296 mg, 0.57 mmole) was dissolved in anhydrous methylene chloride (5 ml). Methyl fluorosulfate (277 μl, 3.4 mmole) was added and the mixture was stirred at room temperature for 5 hours. Anhydrous ether (25 ml) was added and the precipitated [2,6-dimethoxy-4-(benzyloxycarbonyl amino)methyl]phenyl-acridinium-9-carboxylate fluorosulfonate (46) was filtered and washed with ether and dried (yield=99%).

The acridinium (46) (107 mg, 0.169 mmole) was suspended in anhydrous methylene chloride (2 ml). Chlorosulfonic acid (53 μl, 92 mg, 0.797 mmole) was added after the flask was cooled in a dry ice/CCl₄ bath. It was stirred for 30 minutes and the bath was removed. After further stirring at room temperature for 1.5 hours anhydrous ether (20 ml) was added. The precipitated product was filtered and dried in vacuo. The (2,6-dimethoxy-4-aminomethyl-3-chlorosulfonyl)phenyl-acridinium-9-carboxylate fluorosulfonate (47) was directly used in the next reaction.

The sulfonyl chloride (47) (129 mg) was stirred at room temperature in a mixture of methanol (12.5 ml) and water (12.5 ml) for 3 hours. Acetonitrile (35 ml) was added and the solvents were evaporated. The residue was dried in vacuum over phosphorous pentoxide. The (2,6-dimethoxy-4-aminomethyl-3-oxosulfonyl)phenyl-acridinium-9-carboxylate fluorosulfonate (48) was used directly for the next reaction. The same results may be achieved by crystallization from acetonitrile by the addition of ethyl acetate. Other useful solvent combinations include alcohol and ether, such as methanol, ethanol or propanol and diethyl ether (ether is the precipitating solvent). In addition, compound (41) may be further treated with thionyl chloride, as indicated above, to increase the sulfonyl content of the compound, if desired.

Progesterone hemisuccinate (90 mg, 0.209 mmole) and N-methylmorpholine (22 μl, 209 mmole) were dissolved in anhydrous DMF (2 ml). The solution was chilled in dry ice/CCl$_4$ bath and isobutylchloroformate (30 μl, 0.229 mmole) was added. After 2 minutes a solution of the acridinium (42) (101 mg, 0.143 mmole) in dimethylsulfoxide (2 ml) containing N-methylmorpholine (3.14 μl, 0.28 mmole) was added. Stirring was continued at −20° C. for 10 minutes and the cooling bath was removed. After stirring at room temperature for 7 hours, 3 drops of water were added. The solvents were removed in vacuo and ethyl acetate was added to the residue. The oily precipitate was washed repeatedly with ethyl acetate. Upon trituration with acetonitrile (2 ml) the oil separated as solids. The product was purified on HPLC using C$_{18}$ Dynamax semi-prep column (10 mm×250 mm) (commercially available from Rainin Instrument Co., Inc., Woburn, Mass.) using CH$_3$CN/H$_2$O (0.1% trifluoroacetic acid), 55/45 as mobile phase at a flow rate of 2.75 ml/min. The peak appearing at retention time of 6.00 minutes was collected. Evaporation of solvents gave the conjugate (43) (yield=30%). MS: FAB, thioglycerol matrix, 895 (M+, without any counterions).

The progesterone conjugate (49) (1.1 mg) in a mixture of CH$_3$CN (1 ml) and H$_2$O (200 μl) was treated with β-D-thioglucose (0.29 mg) as a solution in water (72 μl). After 10 minutes the solvents were removed completely under vacuum to provide the β-D-thioglucose adduct depicted above.

EXAMPLE 4

The following procedure for attaching to protein is generally applicable to moieties of the present invention.

Mouse IgG (Sigma, 1 mg) was dissolved in 0.9 ml phosphate buffer (100 mM, pH 8.0, 150 mM). If desired, higher pH may be employed, such as a pH as high as 9.5. The solution was then divided into three equal portions of 0.33 mg/0.3 ml (0.0022 μmoles). About 0.3 mg of a moiety of the present invention was dissolved in about 0.4 ml DMF so as to obtain 0.022 moles of moiety in 15 μl DMF.

0.022 μmoles of the compound of the present invention was mixed with 0.0022 μmoles of IgG in a plastic microcentrifuge tube. After 15 minutes, an additional 0.022 μmoles of compound was added to the microcentrifuge tube (compound to protein molar ratio was 20:1). After an additional 15 minutes, excess amounts of the compound of the present invention were quenched with lysine HCl solution (10 μl in 100 mM p$_i$ buffer, pH 8.0) for 15 minutes.

Alternatively, aliquots of 0.0055 μmoles of the compound of the present invention was used instead of 0.022 μmoles (compound to protein molar ratio was 5:1).

Biorad glass columns (1 cm×50 cm) (commercially available from Biorad, Chemical Division, Richmond, Calif.) were packed with previously swelled and deaerated Sephadex G-50-80 in phosphate buffer (100 mM, pH 6.3, 150 mM NaCl, 0.001% TMS) to a bed volume of 45 ml. The reaction solution was run through the columns at a flow rate of 0.3-0.4 ml/min. 0.5 ml fractions were collected. Labelled protein fractions were detected by diluting 20 μl from each fraction to 1 ml and determining the chemiluminescence produced with 30 μl of the diluted solution. Labelled fractions were then pooled.

The pooled conjugate fractions were dialyzed to improve the purity of immunoreactive conjugate. The pooled fractions were dialyzed against 500 ml pH 6.3 phosphate buffer (100 mM, pH 6.3, 150 mM NaCl, 0.001% TMS) over a period of 24 hours with three buffer changes.

EXAMPLE 5

Moieties containing an unreduced heterocyclic ring or ring system can be converted to their equivalent reduced forms while such unreduced moieties are attached to protein or other material. This can be accomplished by using a reducing agent such as sodium cyanoborohydride. The procedure for reduction of an acridinium/IgG conjugate is described below. The same procedure is applicable to the reduction of other conjugates.

The IgG labelled with a representative acridinium (100 μg) in phosphate buffer (400 μl) (pH 6.0, 100 mM, 150 mM, NaCl, 0.001% Thimerosal) was treated with a freshly prepared solution (10 μl) containing sodium cyanoborohydride (10–7 moles). After two hours of incubation at room temperature the conversion of the acridinium label on the antibody to the acridan is complete as seen from the UV-Vis spectra indicating appearance of a band at 280 nm and disappearance of the band at 360 nm. This reduced form retained all immunological properties.

EXAMPLE 6

ASSAY PROTOCOLS

1. Components
A) Progesterone Conjugate of the b-D-thioglucose adduct of (2,6-dimethoxy-3-chlorosulfonyl)phenyl-N-methyl-acridinium-9-carboxylate fluorosulfonate: 20 pg/ml progesterone conjugate in phosphate buffer (pH 6.0, 100 mM phosphate, 150 mM NaCl, 0.1% human serum albumin, 0.001% Thimerosal).
B) Primary antibody: Rabbit anti-progesterone (Cambridge Medical Diagnostics) in phosphate buffer (pH 6.0, 200 mM phosphate, 150 mM NaCl, 0.1% human serum albumin, 0.01% CHAPS, 5 μg Danazol).
C) Solid-phase coated tubes: Dried Nunc® tubes coated with 2.5 μg of Goat anti-Rabbit fc and blocked with 0.5% BSA. Tubes were prepared as follows:
  1) Tubes were ncubated for 1 hour with 2.5 μg/ml Goat anti-Rabbit fc (500 μl) at room temperature.

2) Tubes were washed 3 times with distilled water.
3) Tubes were immediately incubated for 3 hours with 0.5% BSA (500 μl) at room temperature.
4) Tubes were washed 3 times with distilled water.
5) Tubes were dried overnight at 40% relative humidity at room temperature.
6) Tubes were stored in plastic freezer bags at 4° C.
D) Serum matrix: Antech steer serum.
E) Standards: 0, 0.13, 0.38, 1.31, 7.31 16.6 and 37.0 ng/ml.

2. Assay Protocol
1) 50 μl of sample or standard was pipetted into the antibody-coated tubes.
2) 100 μl of conjugate buffer was added.
3) 100 μl of primary antibody buffer was added.
4) Tubes were vortexed gently.
5) Tubes were incubated for 2 hours at 37° C.
6) Tubes were decanted and washed with 150 mM NaCl in 0.1% Tween (1 ml) and then 3 times with distilled water.
7) Tubes were inverted and allowed to drain.
8) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Praire, Minn.).

EXAMPLE 7

A preferred chemiluminescent moiety of the present invention having an $R_nX$ group on the carbon to which the ester linkage is attached is (2,6-dimethoxy-3-chlorosulfonyl)phenyl-N-methyl-acridan-9-ethoxy-9-carboxylate, which has the following formula:

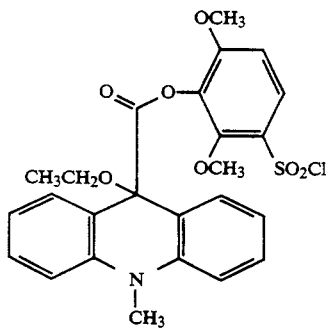

The compound (2,6-dimethoxy-3-chlorosulfonyl)phenyl-N-methylacridan-9-ethoxy-9-carboxylate was synthesized from (2,6-dimethoxy-3-chlorosulfonyl)phenyl-N-methyl-acridinium-9-carboxylate by two alternative methods described below.

1. High Performance Liquid Chromatography (HPLC)

A $C_{18}$ column (Rainin, Dynamax 60 Å, 250 mm × 10 mm) was equilibrated with a mixture of ethanol and acetonitrile (up to 10%) containing about 0.05% of a tertiary amine (e.g., triethylamine). (2,6-dimethoxy-3-chlorosulfonyl)phenyl-N-methyl-acridinium-9-carboxylate was dissolved in the mobile phase and injected onto the column. The major fraction, eluting with a maximum absorbance at 280 nm, was collected at a flow rate of 2.0–2.5 ml/min. The solvent was immediately completely removed under vacuum. The residue was then treated with a small amount of benzene to remove traces of alcohol and to remove moisture from the final product, (2,6-dimethoxy-3-chlorosulfonyl)phenyl-N-methyl-acridan-9-ethoxy-9-carboxylate. This HPLC method is the preferred method of synthesis, since it yields a much purer product. However, the HPLC method may not be appropriate for certain nucleophiles. Where the HPLC method does not work, the nucleophilic anion method described below can be used.

2. Treatment of Starting Compound with Nucleophilic Anion

The compound (2,6-dimethoxy-3-chlorosulfonyl)phenyl-N-methyl-acridinium-9-carboxylate (0.013 mmole, 7.5 mg) was dissolved in absolute ethanol (3 ml) under nitrogen. A solution of potassium-t-butoxide in absolute ethanol (2 mg/ml) was added dropwise (using a gas tight syringe) to the vigorously stirred (2,6-dimethoxy-3-chlorosulfonyl)phenyl-N-methyl-acridinium-9-carboxylate solution until the yellow color of the solution was completely discharged. The ethanol was then completely removed under vacuum. The residue was treated with anhydrous ether (2 ml) and approximately 1 gram anhydrous sodium sulfate. Separation of the ether solution and evaporation of the solvent yielded (2,6-dimethoxy-3-chlorosulfonyl)phenyl-N-methyl-acridan-9-ethoxy-9-carboxylate as a white solid (2.5 mg).

The compound (2,6-dimethoxy-3-chlorosulfonyl)-phenyl-N-methyl-acridan-9-methoxy-9-carboxylate was produced using both the HPLC and nucleophilic anion synthetic procedures from (2,6-dimethoxy-3-chlorosulfonyl)phenyl-N-methyl-acridinium-9-carboxylate. (2,6-dimethyl-3-chlorosulfonyl)phenyl-N-methyl-acridan-9-methoxy-9-carboxylate was produced using the nucleophilic anion synthetic method from (2,6-dimethyl-3-chlorosulfonyl)phenyl-N-methyl-acridinium-9-carboxylate.

The synthetic procedures described herein can be used to produce any of the compounds of the present invention having an $R_nX$ group. If a nucleophile other than ethanol is to donate the $R_nX$ group, the desired nucleophile is substituted for ethanol in the synthetic procedures. If a different acridinium, phenanthridinium, etc. is desired, the compound to which the $R_nX$ group is to be added can be substituted for (2,6-dimethoxy-3-chlorosulfonyl)phenyl-N-methyl-acridinium-9-carboxylate in the synthetic procedures described above. In many instances, a change in the nucleophile will also require a change in solvent (e.g., if methanol is the desired nucleophile, ethanol cannot be used as a solvent because of competition for addition). In such instances, the new nucleophile can be used as a replacement solvent, if appropriate, or a non-nucleophilic, non-protic solvent (e.g., THF) can be substituted.

Other synthetic methods, including without limitation treatment with a nucleophilic solvent, can also be used to produce moieties having an $R_nX$ group.

EXAMPLE 8

The compound (2,6-dimethoxy-3-chlorosulfonyl)-phenyl-N-methyl-acridan-9-ethoxy-9-carboxylate was used as a label in an assay for TSH as follows:

1. Components
A) Labelled Ab: Affinity purified goat anti-TSH was conjugated to (2,6-dimethoxy-3-chlorosulfonyl)phenyl-N-methyl-acridan-9-ethoxy-9-carboxylate as follows: a solution of the anti-TSH antibody (approximately 100 μg) in bicarbonate buffer (0.1M, pH 9.6) was treated with 25 moles excess of (2,6-dimethoxy-3-chlorosulfonyl)phenyl-N-methyl-acridan-9-ethoxy-9- carboxylate as a solution in DMF. The reaction mixture was purified on a fast flow Sephadex G25 (superfine) column (Pharmacia, infra) using an HPLC system. The protein peak was collected at a flow rate of approximately 0.75 ml/min with a mobile phase of phosphate buffer (pH 6.0) containing approximately 20% ethanol. After buffer exchange the labelled antibody preparation was diluted with storage buffer to provide approximately 100,000 counts/100 μl in a LumaTag ™ Analyzer after 1:10 dilution.

B) Storage buffer: 100 mM phosphate, 0.145M NaCl, 0.001% Thimerosal, 0.4% BSA, 0.1 mg/ml mouse g-globulins, and 0.1 mg/ml goat g-globulins, pH 6.0.

C) Capture antibody: Monoclonal-anti-TSH (2 μg/ml) as a solid phase on Nunc ® tubes. Procedure for preparation of solid-phase Nunc ® tubes:
1) 0.4 ml of the capture antibody at 2 μg/ml in PBS buffer (phosphate buffer saline, pH 7.2–7.4, 10 mM phosphate, 100 mM NaCl, 10 mM $NaN_3$) was added to each tube.
2) Tubes were incubated for 18–24 hours.
3) Tubes were washed 3 times with the PBS buffer.
4) Tubes were blocked with 2.0% BSA in PBS buffer and incubated for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum.0, 0.05, 0.1, 0.5, 2.5, 10, 25 and 50 μIU/ml E) Wash Solution: saline buffer containing BSA 2. Assay Protocol
1) 200 μl of sample was pipetted into the coated tubes.
2) 100 μl of labelled antibody was added.
3) Tubes were vortexed gently.
4) Tubes were incubated for 2 hours at room temperature on a shaker.
5) 1 ml Wash Solution was added to each tube.
6) Tubes were washed using a Biotomic washer (commercially available from Ocean Scientific, Inc., Garden Grove, Calif.
7) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

Addition of $HNO_3$ to the assay mixture containing the labelled antibody causes the $C_9$ ethoxy group to cleave from the acridinium molecule before the chemiluminescent reaction is triggered by the addition of NaOH. A standard curve for the assay is shown in FIG. 35.

EXAMPLE 9

A preferred chemiluminescent moiety of the present invention having an $R_nX$ group on the carbon to which the ester linkage is attached and having a peri substituent is phenyl-N-methyl-1,3-dimethyl-acridan-9-methoxy-9-carboxylate, which has the following formula:

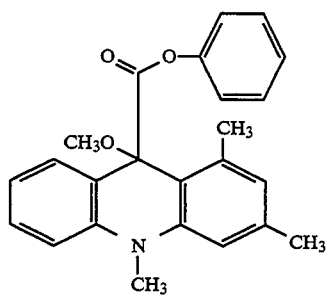

Phenyl-N-methyl-1,3-dimethyl-acridan-9-methoxy-9-carboxylate was synthesized from phenyl-N-methyl-1,3-dimethyl-acridinium-9-carboxylate according to HPLC as described above. To produce phenyl-N-methyl-1,3-dimethyl-acridinium-9-carboxylate, 3,5-dimethylaniline and bromobenzene were reacted under extention Ulmann reaction conditions to obtain the N-phenyl-N-(3,5-dimethyl)phenylamine. Reaction of N-phenyl-N-(3,5-dimethyl)phenylamine with oxalyl chloride provided the intermediate N-phenyl-dimethyl isatin. Upon cyclization under basic conditions, the 1,3-dimethyl-acridine-9-carboxylic acid was formed. The acridine phenyl ester was formed by esterification with phenol as previously described. Phenyl-N-methyl-1,3-dimethyl-acridinium-9-carboxylate was produced from the acridine ester as described above.

I claim:
1. A chemiluminescent compound comprising an aryl ester, thioester or amide of a carboxylic acid substituted heterocyclic ring that is susceptible to chemical attack to dissociate the heterocyclic ring to a transient compound in which the heterocyclic ring is ring carbon-bonded to the carbonyl of the ester, thioester or amide moiety and possesses a heteroatom in an oxidation state that allows chemiluminescence by dissociating a compound that decays to produce chemiluminescence, at the carbon bonded to the carbonyl, the aryl ring is ring carbon-bonded to the oxygen, sulfur or nitrogen of the ester, thioester or amide, as the case may be, and contains at least three substituents on a six-member ring, the substitution on the six-member ring comprises three or more groups acting in concert to sterically and electronically hinder hydrolysis of the ester, thioester or amide linkage, two of said groups are diortho electron donating substitution on the aryl unit in conjunction with meta and/or para substituents that possess a $\sigma_p$ value greater than 0 and less than 1, and an adduct affixed at the carbon atom of the heterocyclic ring to which the ester, thioester or amide carbonyl carbon is directly bonded.

2. A heterocyclic composition capable of chemiluminescent properties when labeled to a specific binding material, by reaction with acid, then peroxide or molecular oxygen, comprising
(a) an aryl ring,
(b) an ester, thioester or amide linkage moiety with enhanced hydrolytic stability, and
(c) a heterocyclic organic ring moiety, in which
(i) the carbonyl carbon of (b) is covalently bonded to a carbon atom (x) of (c) and the remaining free valence of (b) is carbon bonded to an aromatic ring carbon atom (y) of (a), (ii) (a), (c) or both contain at least one sterically-hindering substituent group on the ring carbon atoms adjacent to one or more of (x) and (y), (iii) a monovalent moiety is bonded directly to carbon atom (x), (iv) at least one of (a) and (c) contains a functional group
  (1) directly or indirectly bonded to a ring carbon other than said adjacent carbon atoms to (x) or (y), and
  (2) that is complementary for reaction with a moiety in the specific binding material to effect a heterolytic or homolytic reaction therewith (v) (a) contains one or more substituent groups having a $\sigma_p$ value greater than 0 and less than 1 bonded to ring carbon atoms thereof other than those adjacent to (y), and (vi) (c) contains
  (1) at least one ring carbon atom adjacent to said ring carbon atom (x), and
  (2) a ring member heteroatom in an oxidation state that provides such chemiluminescence properties.

3. The chemiluminescent of claim 1 wherein the heterocyclic ring is from the group consisting of acridinium, benzacridinium, benzacridinium, benzacridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

4. The chemiluminescent composition of claim 2 wherein the heterocyclic ring is from the group consisting of acridinium, benzacridinium, benzacridinium, benzacridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

5. A conjugate possessing chemiluminescent properties by reaction of acid therewith, followed by molecular oxygen or a peroxide, comprising a chemiluminescent label bonded to a specific binding material that contains
  (a) an aryl ring
  (b) a sterically-hindered ester, thioester or amide linkage moiety with enhanced hydrolytic stability, and
  (c) a heterocyclic organic ring, in which
    (i) the carbonyl carbon of (b) is covalently bonded to a carbon atom (x) of (c) and the remaining free valence of (b) is carbon bonded to an aromatic ring carbon atom (y) of (a),
    (ii) (a), (c) or both contain at least one sterically-hindering substituent group on the ring carbon atoms adjacent to one or more of (x) and (y),
    (iii) a monovalent moiety is bonded directly to carbon atom (x),
    (iv) at least one of (a) and (c) contains a functional group
      (1) directly or indirectly bonded to a ring carbon other than said adjacent carbon atoms to (x) or (y), and
      (2) that is complementary for reaction with a moiety in the specific binding material to effect a heterolytic or homolytic reaction therewith
    (v) (a) contains one or more substituent groups having a $\sigma_p$ value greater than 0 and less than 1 bonded to ring carbon atoms thereof other than those adjacent to (y), and
    (vi) (c) contains
      (1) at least one ring carbon atom adjacent to said ring carbon atom (x), and
      (2) a ring member heteroatom that is in an oxidation state whereby reaction of molecular oxygen or a peroxide with said composition forms an intermediate which decays to produce chemiluminescence.

6. Assaying the presence of an analyte in a sample which comprises contacting an analyte with a chemiluminescent labeled specific binding material, inducing chemiluminescence by treating the label with acid, then by decay of an intermediate formable in the presence of peroxide or molecular oxygen, and measuring chemiluminescence therefrom to assay the analyte; wherein the chemiluminescent labeled specific binding material contains
  (a) an aryl ring
  (b) a sterically-hindered ester, thioester or amide linkage moiety with enhanced hydrolytic stability, and
  (c) a heterocyclic organic ring, in which
    (i) the carbonyl carbon of (b) is covalently bonded to a carbon atom (x) of (c) and the remaining free valence of (b) is carbon bonded to an aromatic ring carbon atom (y) of (a),
    (ii) (a), (c) or both contain at least one sterically-hindering substituent group on the ring carbon atoms adjacent to one or more of (x) and (y),
    (iii) a monovalent moiety is bonded directly to carbon atom (x),
    (iv) at least one of (a) and (c) contains a functional group
      (1) directly or indirectly bonded to a ring carbon other than said adjacent carbon atoms to (x) or (y), and
      (2) that is complementary for reaction with a moiety in the specific binding material to effect a heterolytic or homolytic reaction therewith
    (v) (a) contains one or more substituent groups having a $\sigma_p$ value greater than 0 and less than 1 bonded to ring carbon atoms thereof other than those adjacent to (y), and
    (vi) (c) contains
      (1) at least one ring carbon atom adjacent to said ring carbon atom (x), and
      (2) a ring member heteroatom that is in an oxidation state whereby reaction of molecular oxygen or a peroxide with said composition forms an intermediate which decays to produce chemiluminescence.

7. A specific binding assay kit comprising a vial containing a conjugate possessing chemiluminescent properties by reaction therewith of acid, then molecular oxygen or a peroxide, comprising a chemiluminescent label bonded to a specific binding material that contains
  (a) an aryl ring
  (b) a sterically-hindered ester, thioester or amide linkage moiety with enhanced hydrolytic stability, and
  (c) a heterocyclic organic ring, in which (i) the carbonyl carbon of (b) is covalently bonded to a carbon atom (x) of (c) and the remaining free valence of (b) is carbon bonded to an aromatic ring carbon atom (y) of (a), (ii) (a), (c) or both contain at least one sterically-hindering substituent group on the ring carbon atoms adjacent to one or more of (x) and (y), (iii) a monovalent moiety is bonded directly to carbon atom (x), (iv) at least one of (a) and (c) contains a functional group
  (1) directly or indirectly bonded to a ring carbon other than said adjacent carbon atoms to (x) or (y), and
  (2) that is complementary for reaction with a moiety in the specific binding material to effect a heterolytic or homolytic reaction therewith (v) (a) contains one or more substituent groups having a $\sigma_p$ value greater than 0 and less than 1 bonded to ring carbon atoms thereof other than those adjacent to (y), and (vi) (c) contains
  (1) at least one ring carbon atom adjacent to said ring carbon atom (x), and
  (2) a ring member heteroatom that is in an oxidation state whereby reaction of molecular oxygen or a peroxide with said composition forms an intermediate which decays to produce chemiluminescence.

8. A method of preparing a specific binding conjugate in which a chemiluminescent compound containing ester, thioester or amide linkage, that is carbon bonded to a heterocyclic ring therein, is attached to a specific binding material, which comprises
  (a) attaching the chemiluminescent compound to the specific binding material, and
  (b) forming an adduct of the attached chemiluminescent compound at the carbon atom of the heterocyclic ring to which the linkage is attached.

9. The method of claim 8 wherein the adduct comprises
—H
—CN
—OR, where R is alkyl, aryl, an amino acid or a sugar
—NR$_2$, where R is alkyl, aryl, an amino acid or a sugar
—SR, where R is alkyl, aryl, an amino acid or a sugar
—S$_2$R, where R is alkyl, aryl, an amino acid or a sugar.

10. The method of claim 8 wherein the adduct comprises
—CN
—OR, where R is alkyl, aryl, an amino acid or a sugar
—NR$_2$, where R is alkyl, aryl, an amino acid or a sugar
—SR, where R is alkyl, aryl, an amino acid or a sugar or a sugar
—S$_2$R, where R is alkyl, aryl, an amino acid or a sugar
a halogen.

11. The method of claim 8 wherein the adduct comprises a thio glucose.

12. The method of claim 8 wherein the heterocyclic ring comprises acridinium, benz[a]acridinium, benz[b]acridinium, benz[c]acridinium, a 1,24-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidinium, pyridazinium, pyrazinium, phenanthridinium, or quinoxalinium.

13. A labeled specific binding conjugate comprising a chemiluminescent compound that contains an ester, thioester or amide linkage and carbon bonding to a heterocyclic ring therein, attached to a specific binding material, and an adduct of the attached chemiluminescent compound at the carbon atom of the heterocyclic ring to which the linkage is attached.

14. The labeled specific binding conjugate of claim 13 wherein the heterocyclic ring comprises acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidinium, pyridazinium, pyrazinium, phenanthridinium, or quinoxalinium.

15. The labeled specific binding conjugate of claim 13 wherein the label will luminesce in aqueous solution following reaction with hydrogen peroxide or oxygen, and hydroxide.

* * * * *

UNITED STATES PATENT AND TRADEMARK OFFICE
CERTIFICATE OF CORRECTION

PATENT NO. : 5,338,847
DATED : August 16, 1994
INVENTOR(S) : McCapra

It is certified that error appears in the above-indentified patent and that said Letters Patent is hereby corrected as shown below:

In column 33, line 27, change the first word "benzacridinium" to read ---benz[a]acridinium---.
In column 33, line 27, change the second word "benzacridinium" to read ---benz[b]acridinium---.
In column 33, lines 27-28, change the third word "benzacridinium" which is before "a 1,2,4,-triazole" on line 28, to read ---benz[c]acridinium---.

In column 33, line 36, change first full word "benzacridinium" to read ---benz[a]acridinium---.
In column 33, line 36, change second full word "benzacridinium" to read ---benz[b]acridinium---.
In column 33, lines 36-37, change word "benzacrdinium" which is before "a 1,2,4-triazole" on line 37, to read ---benz[c]acridinium---.

Signed and Sealed this

Twenty-seventh Day of December, 1994

Attest:

BRUCE LEHMAN

*Attesting Officer*      *Commissioner of Patents and Trademarks*